United States Patent [19]
Tsukada

[11] Patent Number: 5,897,527
[45] Date of Patent: Apr. 27, 1999

[54] PORTABLE ANALGESIC SYSTEM

[75] Inventor: Osamu Tsukada, Nagano, Japan

[73] Assignee: Tsukada Medical Research Co., Ltd., Tokyo, Japan

[21] Appl. No.: 08/704,739
[22] PCT Filed: Jun. 6, 1995
[86] PCT No.: PCT/JP95/01108
§ 371 Date: Sep. 5, 1996
§ 102(e) Date: Sep. 5, 1996
[87] PCT Pub. No.: WO96/39210
PCT Pub. Date: Dec. 12, 1996
[51] Int. Cl.[6] .................................................. A61M 37/00
[52] U.S. Cl. .......................... 604/82; 604/890.1; 604/19; 604/48; 604/83; 604/248
[58] Field of Search .................................... 604/82, 890.1, 604/19, 48, 65, 67, 83, 85, 248, 253, 410

[56] References Cited

U.S. PATENT DOCUMENTS 5,605,545  2/1997  Nowosielski et al. .................. 604/118
5,658,271  8/1997  Loubser ................................... 604/410

Primary Examiner—Mark Bockelman
Assistant Examiner—N. Kent Gring
Attorney, Agent, or Firm—Sughrue, Mion, Zinn, Macpeak & Seas, PLLC

[57] ABSTRACT

A portable analgesic system comprises a liquid medicine supply unit which stores a given amount of liquid medicine temporarily and then discharges the liquid medicine automatically, a first three-way connector connected to an outlet of the liquid medicine supply unit, an intermittent injection line for liquid medicine connected to one outlet of the first three-way connector, a continuous injection line for liquid medicine connected to the other outlet of the first three-way connector, and a second three-way connector for intercommunicating with outlets of the both lines.

4 Claims, 6 Drawing Sheets

PORTABLE ANALGESIC SYSTEM

TECHNICAL FIELD

This invention relates to a portable analgesic system which can be attached to a patient's body.

BACKGROUND ART

An analgesic plays an important role in pain control and especially in cases involving chronic pain. It has heretofore been necessary for a patient to be hospitalized for a long time or to visit a hospital as an out-patient The need for frequent injection of liquid medicine such as an analgesic or the like is onerous both to a patient and in terms of time and efficiency to a hospital. Consequently, an automatic injection system has been developed which injects liquid medicine to an in-patient periodically and automatically. However, conventional systems are large, expensive, and physically limit a patient.

Therefore, a convenient automatic injection system which is not physically limiting and can be applied to in patients, out-patients, and home-patients has been desired for a long time.

Thus, the applicant has proposed a portable analgesic system (PCT/JP94/00608) which satisfies the above requirements This portable analgesic system comprises a continuous injection for liquid medicine which discharges liquid medicine continuously for a given period of time; a switch valve connected to an outlet of said injector for shutting off discharge of liquid medicine from said injector; a three-way connector to an outlet of said switch valve and having three ways; a flexible reservoir connected to one way of said three-way connector for storing liquid medicine; and a pressure-check valve connected to another way of said three-way connector for opening a flow passage only when a pressure of liquid medicine in said reservoirs rises above a given value.

In the portable analgesic system, a continuous injector for liquid medicine which has a given capacity and a given self-maintaining discharge time is prepared beforehand and a given kind and amount of liquid medicine is injected into the injector in accordance with the condition of a patient. Then, the switch valve is opened to transfer liquid medicine to the reservoir for a given period of time. During such a transference of medicine, a patient can freely move with the system being attached to the body.

A period of time for transferring liquid medicine from the injector to the reservoir coincides with a self-maintaining remedy effect time of liquid medicine. When pain is felt, a patient compresses the reservoir to inject the liquid medicine contained in the reservoir into the body through the pressure-check valve.

In preparation for any subsequent pain, the injector can then be supplied with liquid medicine by a licensee either at the patient's home or at a hospital.

This system has a distinctive effect on the specific condition of patient's disease. However, there are intermittent occasions when the injection of a given amount of liquid medicine into a patient's body is required and therefore administered, e.g., when the patient experiences an irregular or sudden pain. This occurs in parallel with the periodical continuous injection for liquid medicine and in accordance with the ingravescence of the state of the disease, the state of the affected body part and the like.

In this case, a continuous injector for liquid medicine is used in parallel with the portable analgesic system described above. Such a continuous injector for liquid medicine has been developed (Japanese Patent No. 1384289) by the present applicant. This injector includes an inlet portion for liquid medicine, an outlet portion for liquid medicine, and a balloon which connects the inlet portion to the outlet portion. Liquid medicine injected in the balloon flows out through the outlet portion for a long period of time.

However, when using the portable analgesic system in parallel with the continuous injector for liquid medicine, it is necessary to attach to a patient's body two continuous supply units which have substantially the same structures. This is onerous to a doctor or a nurse and is an encumbrance to a patient.

DISCLOSURE OF INVENTION

An object of the present invention is to provide a portable and convenient analgesic system which is attached to a patient's body and can inject liquid medicine into the patient's body periodically, for a long time, and at irregular intervals as required by a patient.

In order to achieve the above objective, a portable analgesic system comprises: a liquid medicine supply unit which stores a given amount of liquid medicine temporarily and then discharges the liquid medicine automatically; a first three-way connector connected to an outlet of the liquid medicine supply unit; an intermittent injection line for liquid medicine connected to one outlet of the first three-way connector; a continuous injection line for liquid medicine connected to the other outlet of the first three-way connector; and a second three-way connector for intercommunicating outlets of both lines.

The liquid medicine supply unit includes a balloon made of an elastic material, an inlet portion for liquid medicine provided on one end of the balloon, an outlet portion for liquid medicine provided on the other end of the balloon, and a protective cover for enclosing the balloon.

The intermittent injection line for liquid medicine includes a first flow rate controller for controlling a flow rate of liquid medicine, a switch valve connected to an outlet of the first controller for shutting off discharge of liquid medicine from the first controller; a third three-way connector connected to an outlet of the switch valve and having three ways; a flexible reservoir connected to one way of the third three-way connector for storing liquid medicine; and a pressure-check valve connected to another way of the third three-way connector for opening a flow passage only when a pressure of liquid medicine in the reservoirs rises above a given value.

The continuous injection line for liquid medicine includes a second flow rate controller for controlling flow rate of liquid medicine.

In the portable analgesic system of the present invention, the liquid medicine supply unit and first and second flow rate controllers have a given capacity and given self-maintaining discharge time which is prepared beforehand with the result that a given kind and amount of liquid medicine is injected into the supply unit according to the condition of a patient. Then, the liquid medicine is continuously injected, through the continuous injection line, into a patient's body for a long time. Meanwhile, the switch valve in the intermittent injection line is open to transfer liquid medicine to the reservoir for a given period of time. During this period, the patient can freely move with the system attached to the body.

The period of time for transferring liquid medicine from the supply unit to the reservoirs essentially coincides with a self-maintaining remedy effect time of the liquid medicine.

However, when the patient feels pain suddenly, the reservoir can be compressed to inject the liquid medicine contained in the reservoir into the patient's body through the pressure-check valve. Thus, temporary relief from pain is provided.

In preparation for the next continuous analgesic process and intermittent assuagement of any sudden pain, the supply unit can be refilled with liquid medicine by licensee at the patient's home or a hospital

BEST MODE FOR CARRYING OUT THE INVENTION

An embodiment of a portable analgesic system of the present invention will be explained below by referring now to FIGS. 1 through 6.

Figure 1:
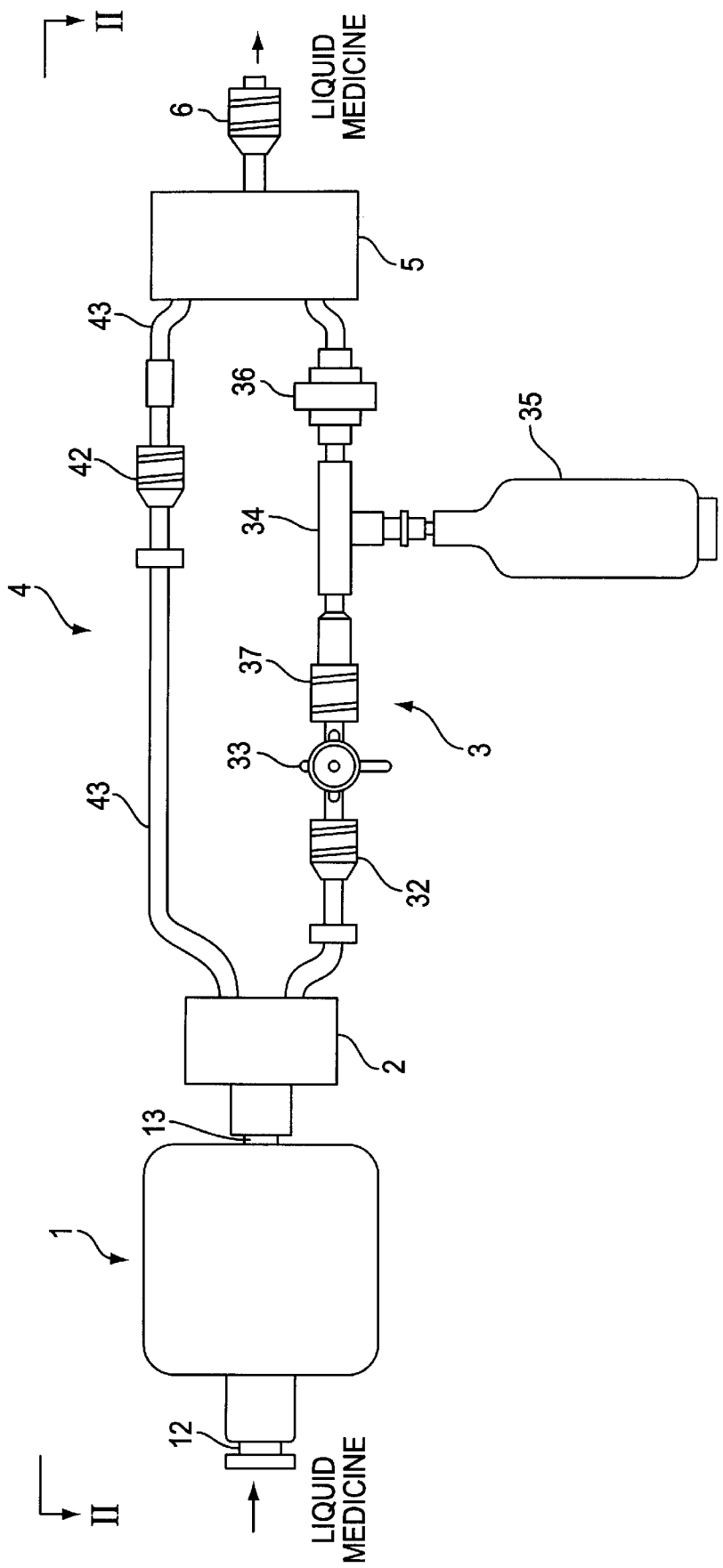
FIG. 1 is a plan view of a portable analgesic system of the present invention.
Figure 2:
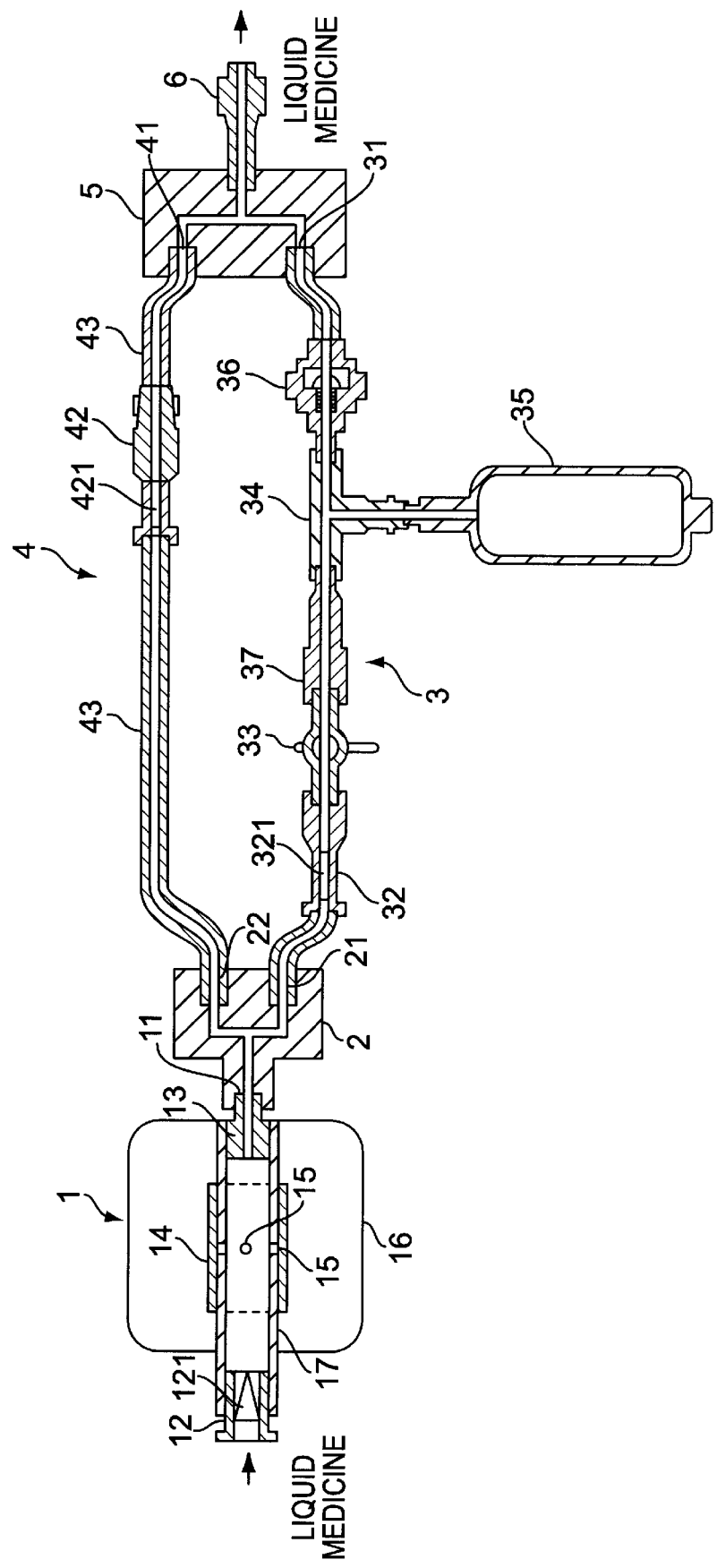
FIG. 2 is a longitudinal cross sectional view of the system taken along line II—II in FIG. 1.

As shown in FIGS. 1 and 2, a portable analgesic system of the present invention comprises: a liquid medicine supply unit 1 which stores a given amount of liquid medicine temporarily and then discharges the liquid medicine automatically; a first three-way connector 2 connected to an outlet 11 of the liquid medicine supply unit 1; an intermittent injection line 3 for liquid medicine connected to one outlet 21 of the first three-way connector 2; a continuous injection line 4 for liquid medicine connected to the other outlet 22 of the first three-way connector 2; and a second three-way connector 5 for intercommunicating outlets 31 and 41 of the both lines 3 and 4.

The liquid medicine supply unit 1 includes a balloon 14 made of an elastic material, an inlet portion 12 for liquid medicine provided on one end of the balloon, an outlet portion 13 for liquid medicine provided on the other end of the balloon 14, and a protective cover 16 for enclosing the balloon 14. More particularly, the liquid medicine supply unit 1 is provided on opposite ends of a cylindrical body 17 with an inlet portion 12 for liquid medicine and an outlet portion 13 for liquid medicine. A balloon 14 is attached to an outer periphery of the cylindrical body 17 An interior of the balloon 14 is connected to an interior of the cylindrical body 17 through a communication hole 15.

The cylindrical body 17 may be omitted and the inlet portion 12 and outlet portion 13 may be directly interconnected.

The inlet portion 12 is provided with a check valve 121 which prevents injected liquid medicine from flowing in a reverse direction. The balloon 14 is made of an elastic material and can accommodate a given amount of liquid medicine. In order to protect the balloon 14 under its inflation against an external force, a safety cover 16 is attached to the injector 1.

As shown in FIG. 2, the intermittent injection line 3 for liquid medicine includes a first flow rate controller 32 for controlling a flow rate of liquid medicine, a switch valve 33 connected to an outlet of the first controller 32 for shutting off discharge of liquid medicine from the first controller 32; a third three-way connector 34 connected to an outlet of the switch valve 33 and having three ways; a flexible reservoir 35 connected to one way of the third three-way connector 34 for storing liquid medicine; and a pressure-check valve 36 connected to another way of the third three-way connector 34 for opening a flow passage only when a pressure of liquid medicine in the reservoir 35 rises above a given amount.

Preferably, the switch valve 33 and third three-way connector 34 are coupled through a female lure connector 37 to each other while a male lure connector 6 is connected to an outlet 31 of the pressure-check valve 36 through the second three-way connector 5. The female lure connector 37 assures the formation of a space for enabling an operation of the switch valve 33 easy. The male lure connector 6 enables easy connection of a catheter and the like to the system. The respective elements may be interconnected by vinyl tubes.

The first flow rate controller 32 is provided with a control path 321 having a minute diameter which controls an outflow period of time for liquid medicine.

The switch valve 33, female lure connector 37, first, second and third, three-way connectors 2, 5 and 34, and male lure connector 6 can be made from products already on the market.

The reservoir 35 is made of a durable and flexible material (for example, polyethylene, polypropylene, and the like) and formed into a ball, bellows, cylinder or the like. The detachable reservoir 35 is attached to the third threeway connector 34 anticipating breakage, pollution, or the like.

The pressure-check valve 36 is, for example, preferably made from an umbrella valve on the market. The umbrella valve is closed normally and opened when an internal pressure rises over a given value, for example, about 250 mmHg. This pressure-setting does not actuate the umbrella valve under an injection pressure of liquid medicine to the reservoir 35 (about 100–200 mmHg) but is below a pressure caused upon compression of the reservoir 35 which is filled with liquid medicine (about 350–400 mmHg).

As shown in FIG. 2, the continuous injection line 4 for liquid medicine includes a second flow rate controller 42 for controlling a flow rate of liquid medicine. The second flow rate controller 42 is provided with a control path 421 having a minute diameter which controls an outflow period of time for liquid medicine. The respective elements in the line 4 may be interconnected through vinyl tubes 43 and the like having appropriate length so that both lines 3 and 4 are of approximate equal lengths and the lengths are adjustable.

Next, an operation of the portable analgesic system of the present invention will be explained by referring to FIGS. 3 through 6.

Figure 3:
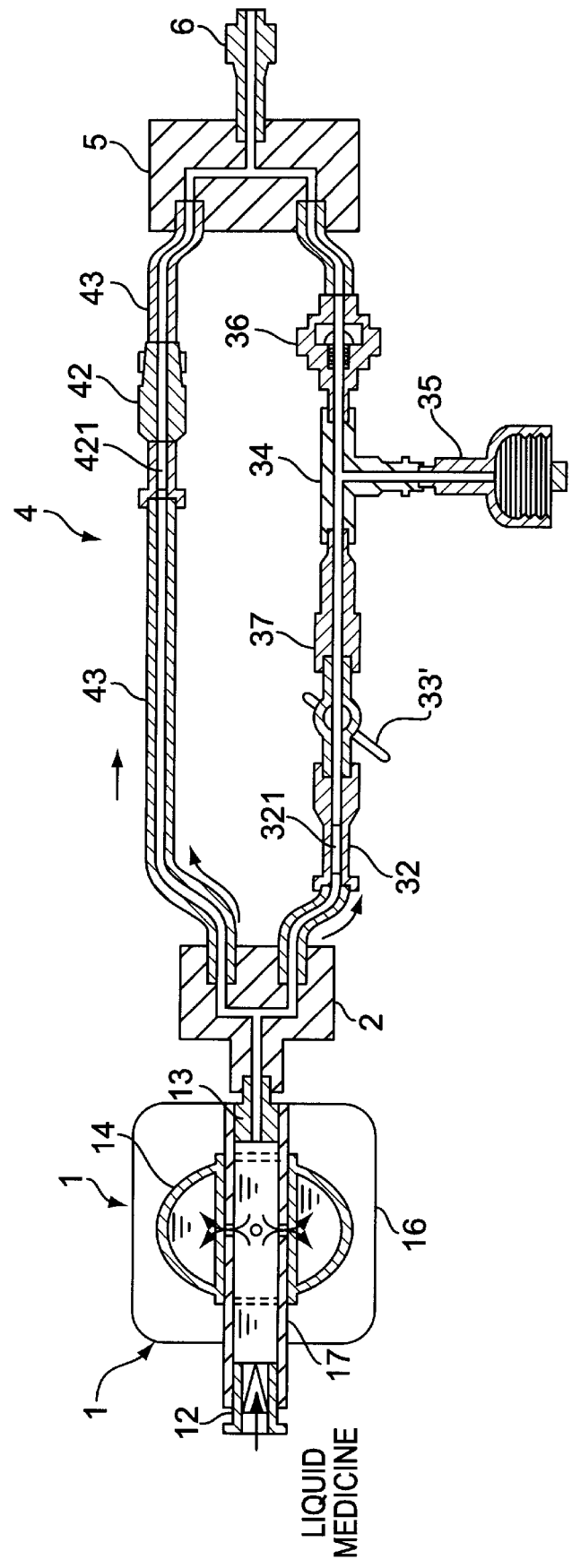
FIG. 3 is an explanatory view illustrating an operation of injecting liquid medicine into a supply unit for liquid medicine.

First, as shown in FIG. 3, the switch valve 33 is closed, the reservoir 35 is compressed to the minimum volume, and a given amount of liquid medicine (for example, physiological saline, grape sugar, antibiotic substance, calmative, analgesic, heparin, nitroglycerin solution and the like) is injected into the liquid medicine supply unit 1 through the inlet portion 12 by an injector or the like (not shown).

The capacity and discharge-maintaining period of time of the supply unit 1 is selected beforehand in accordance with the condition of the patient After the preparation described above, the system of the present invention is secured to the patient and the male lure connector 6 communicates with the interior of the patient's body by means of a catheter or the like (not shown). Alternately, the above injection of liquid medicine may be carried out after the present system has been secured to the patient's body.

Figure 4:
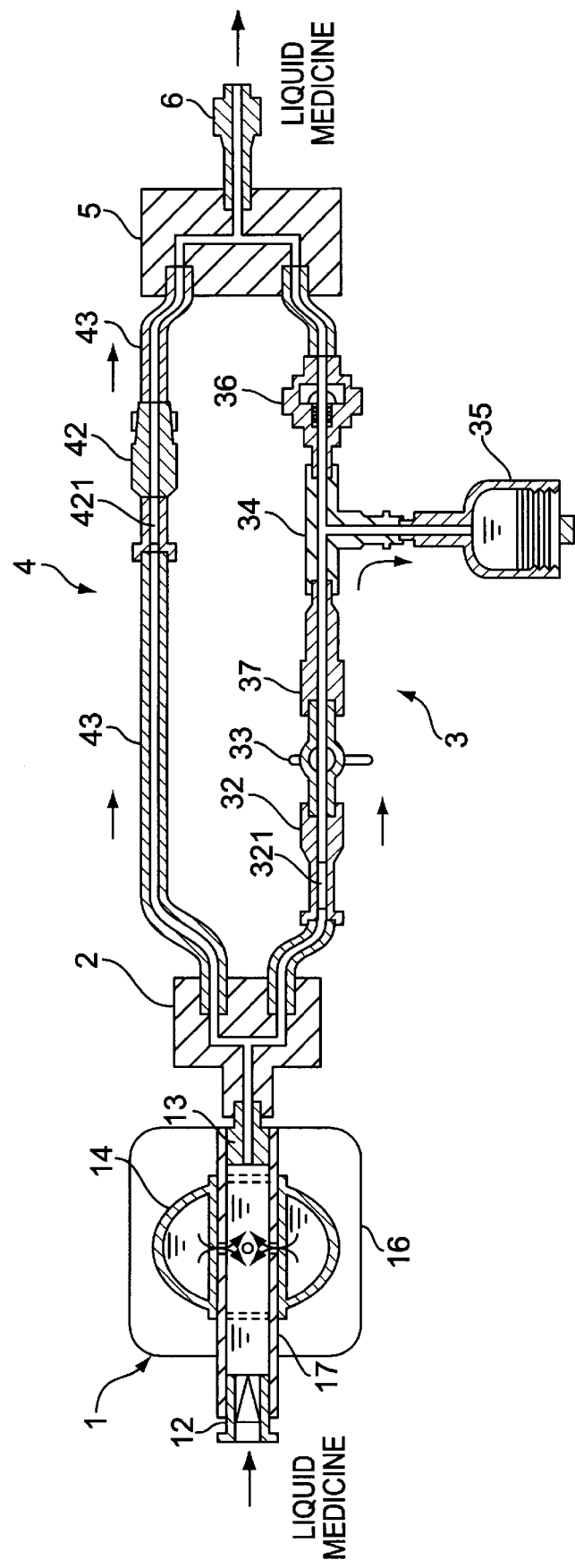
FIG. 4 is an explanatory view illustrating an operation of transferring the liquid medicine from the supply unit to a continuous injection line for liquid medicine, an operation which takes place simultaneously with the transferal of the liquid medicine from the supply unit to a reservoir in an intermittent injection line for liquid medicine.

Next, as shown in FIG. 4, the switch valve 33 is open. Little by little, the liquid medicine accumulates in the reservoir 35 and is stored for a long period of time (for example, 0.05–10 hours) through the outlet portion 13, first three-way connector 2, control path 321 of the first flow rate controller 32, switch valve 33 female lure connector 37, second three-way connector 34 in the line 3 by means of a contraction force of the balloon 14.

On the other hand, the liquid medicine discharged from the supply unit 1 is continuously supplied to the continuous injection line 4 through the first three-way connector 2. The liquid medicine in the line 4 flows through the control path 421 into the second flow rate controller 42, second three-way connector 5, male lure connector 6, then through the catheter (not shown) into the patient's body.

Figure 5:
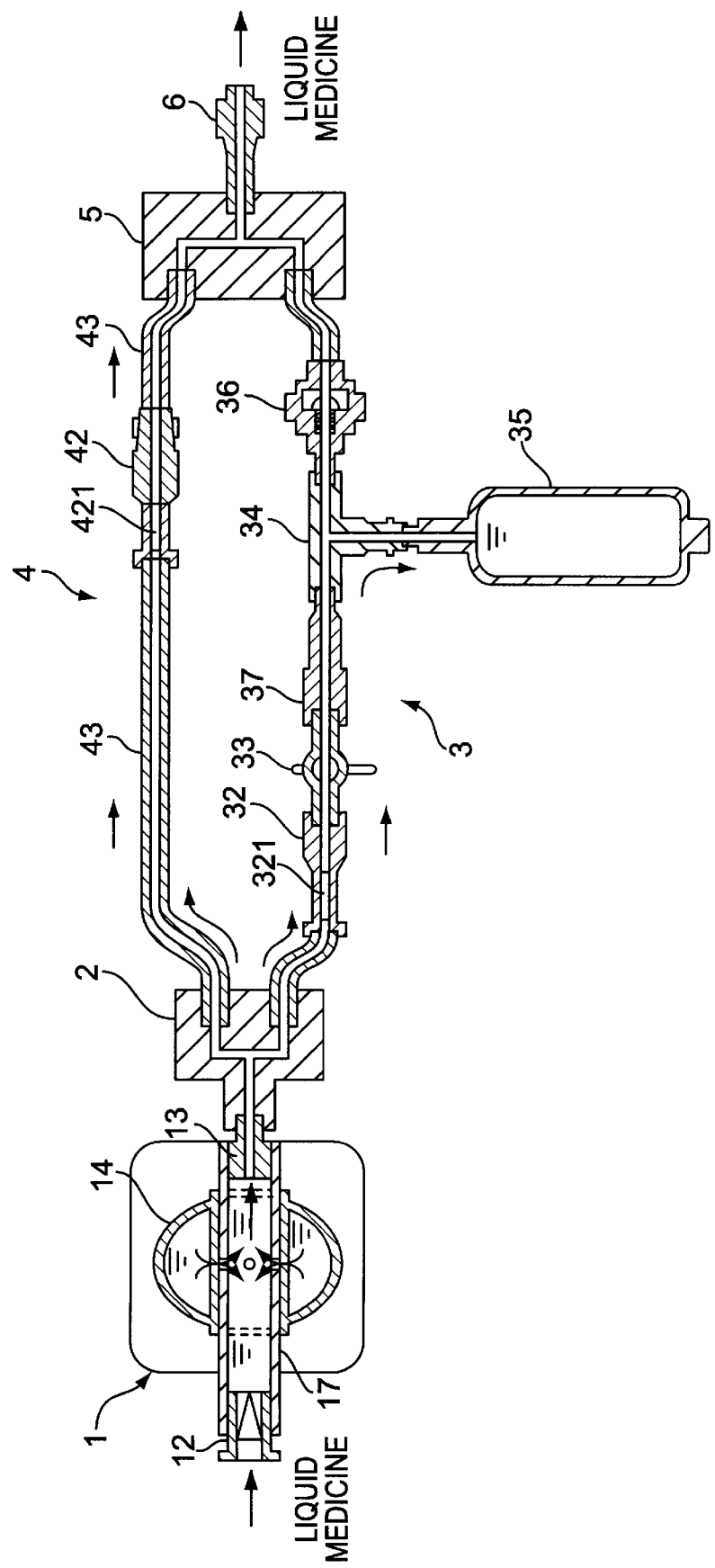
FIG. 5 is an explanatory view of the operation at the final stage of transferring the liquid medicine from the supply unit to the reservoir in the intermittent liquid medicine injection line while the refilling of liquid medicine to the continuous liquid medicine injection line occurs.

Finally, as shown in FIG. 5, a part of the liquid medicine in the balloon 14 is transferred to the reservoir 35. An amount of liquid medicine to be stored in the reservoir 35 can be adjusted by operating the switch valve 33 before the reservoir 35 is filled with liquid medicine. However, since the operation of the switch valve during transferring of liquid medicine must be carried out sometimes under the strict supervision of a doctor, a locking mechanism (not shown) may be provided to bring the switch valve 33 into neutral state of operation during transfer.

Figure 6:
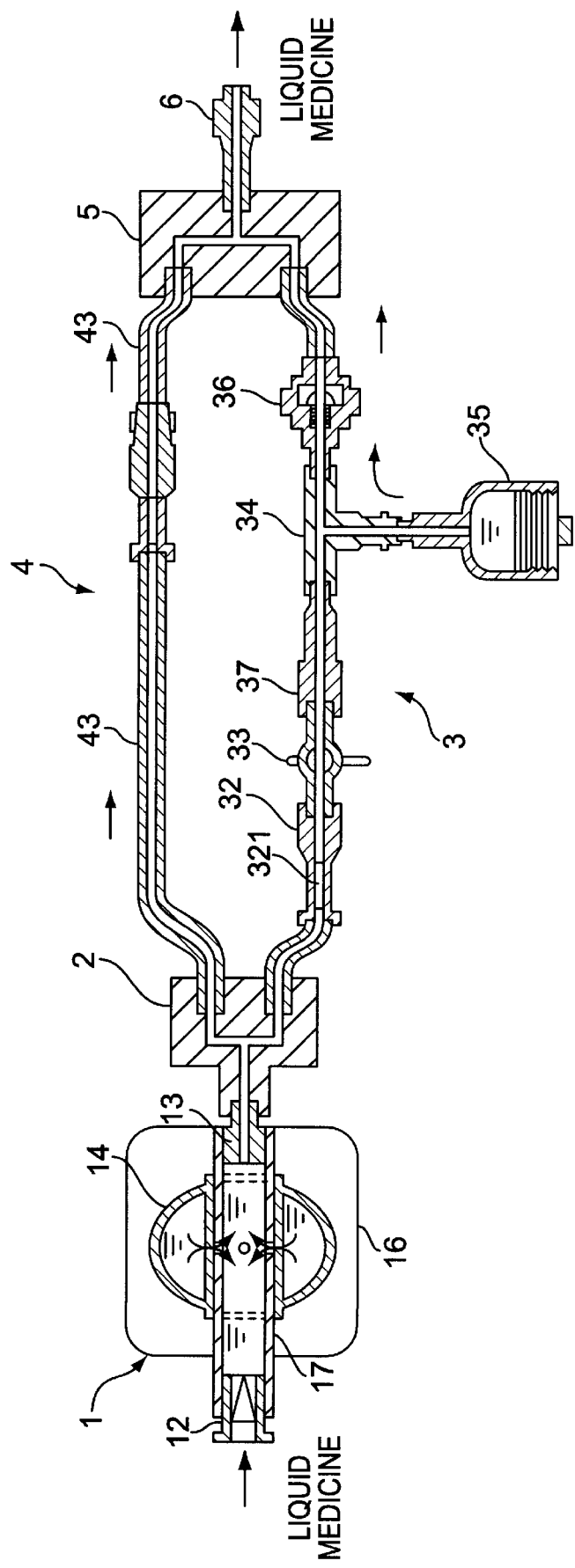
FIG. 6 is an explanatory view illustrating an operation of ejecting the liquid medicine out of the system upon compressing the reservoir in the intermittent liquid medicine injection line during the refilling of the liquid medicine to the continuous liquid medicine injection line.

Thereafter as shown in FIG. 6, when the patient feels sudden pain, by manually compressing the reservoir, the liquid medicine can be ejected from the reservoir 35 through the third three-way connector 34, pressure-check valve 36, and male lure connector 6 to the outside (interior of the patient's body).

The present system can be used again by repeating the above operation

INDUSTRIAL APPLICABILITY

The system of the present invention can be applied in first-aid treatment as well as in chronic conditions involving terminal care. Furthermore, it has applications in the administering of drugs for sedation, detoxification, fever control, supply of nutritional supplements and the like, as well as for analgesics.

I claim:

1. A portable analgesic system comprising: a liquid medicine supply unit which stores a given amount of liquid medicine temporarily and then discharges said liquid medicine automatically; a first three-way connector connected to an outlet of said liquid medicine supply unit; an intermittent injection line for liquid medicine connected to one outlet of said first three-way connector; a continuous injection line for liquid medicine connected to one outlet of said first three-way connector; and a second three-way connector for intercommunicating with outlets of both lines.

2. The portable analgesic system according to claim 1, wherein said liquid medicine supply unit includes a balloon made of an elastic material, an inlet portion for liquid medicine provided on one end of said balloon, an outlet portion for liquid medicine provided on the other end of said balloon, and a protective cover for enclosing said balloon.

3. The portable analgestic system comprising: a liquid medicine supply unit which stores a given amount of liquid medicine temporarily and then discharges said liquid medicine automatically; a first three-way connector connected to an outlet of said liquid medicine supply unit; an intermittent injection line for liquid medicine connected to one outlet of said first three-way connector, a continuous injection line for liquid medicine connected to one outlet of said first three-way connector; and a second three-way connector for intercommunicating outlets of both lines; wherein said intermittent injection line for liquid medicine includes a first flow rate controller for controlling a flow rate of liquid medicine, a switch valve connected to an outlet of said first controller for shutting off discharge of liquid medicine from said first controller; a third three-way connector to an outlet of said switch valve and having three ways; a flexible reservoir connected to one way of said third three-way connector for storing liquid medicine; and a pressure-check valve connected to another way of said third three-way connector for opening a flow passage only when a pressure of liquid medicine in said reservoir rises above a given level.

4. The portable analgesic system according to claim 3, wherein said continuous injection line for liquid medicine includes a flow rate controller for controlling a flow rate of liquid medicine.

\* \* \* \* \*